United States Patent [19]
Arai et al.

[11] Patent Number: 6,018,563
[45] Date of Patent: Jan. 25, 2000

[54] X-RAY IMAGING APPARATUS

[75] Inventors: Yoshinori Arai, Tokyo; Keisuke Mori, Kyoto; Masakazu Suzuki, Kyoto; Akifumi Tachibana, Kyoto, all of Japan

[73] Assignee: J. Morita Manufacturing Corporation, Kyoto, Japan

[21] Appl. No.: 08/986,945

[22] Filed: Dec. 8, 1997

[30] Foreign Application Priority Data

Dec. 10, 1996 [JP] Japan .................................... 8-330065
Sep. 8, 1997 [JP] Japan .................................... 9-242847

[51] Int. Cl.$^7$ ...................................................... A61B 6/02
[52] U.S. Cl. ............................................. 378/39; 378/98.7
[58] Field of Search .................................. 378/38, 37, 40, 378/98.2, 98.7, 98.8, 108, 109, 110, 111, 112

[56] References Cited

U.S. PATENT DOCUMENTS

| | | |
|---|---|---|
| 4,063,099 | 12/1977 | Grassme . |
| 4,815,115 | 3/1989 | Nieminen et al. ........................ 378/38 |
| 4,910,592 | 3/1990 | Shroy, Jr. et al. ..................... 378/98.7 |
| 5,003,572 | 3/1991 | Meccariello et al. .................. 378/98.7 |
| 5,479,468 | 12/1995 | Horbaschek et al. .................. 378/98.2 |
| 5,513,239 | 4/1996 | Mulder .................................. 378/98.7 |
| 5,617,462 | 4/1997 | Spratt .................................... 378/98.7 |
| 5,675,624 | 10/1997 | Relihan et al. ........................ 378/98.7 |

FOREIGN PATENT DOCUMENTS

| | | |
|---|---|---|
| 0629105 | 12/1994 | European Pat. Off. . |
| 19609138 | 9/1996 | Germany . |
| 19611451 | 10/1996 | Germany . |
| WO97/14277 | 4/1997 | WIPO . |

*Primary Examiner*—David P. Porta
*Attorney, Agent, or Firm*—Koda & Androlia

[57] ABSTRACT

An X-ray imaging apparatus including an X-ray tube which emits X-rays, an image sensor which detects X-rays which pass through an object, a support arm which supports the X-ray tube and the image sensor so that they are opposed to each other across the object, a driving motor which moves the support arm in a predetermined direction, a gain adjustment circuit which adjusts the imaging sensitivity of the image sensor and a controlling circuit for controlling the gain of the adjusting circuit. The controlling circuit controls the gain adjusting circuit on the basis of the detected image density of the image sensor. When the adjustment by means of the gain adjusting circuit is insufficient, the controlling circuit controls X-ray tube current, X-ray tube voltage and driving speed adjusters.

5 Claims, 11 Drawing Sheets

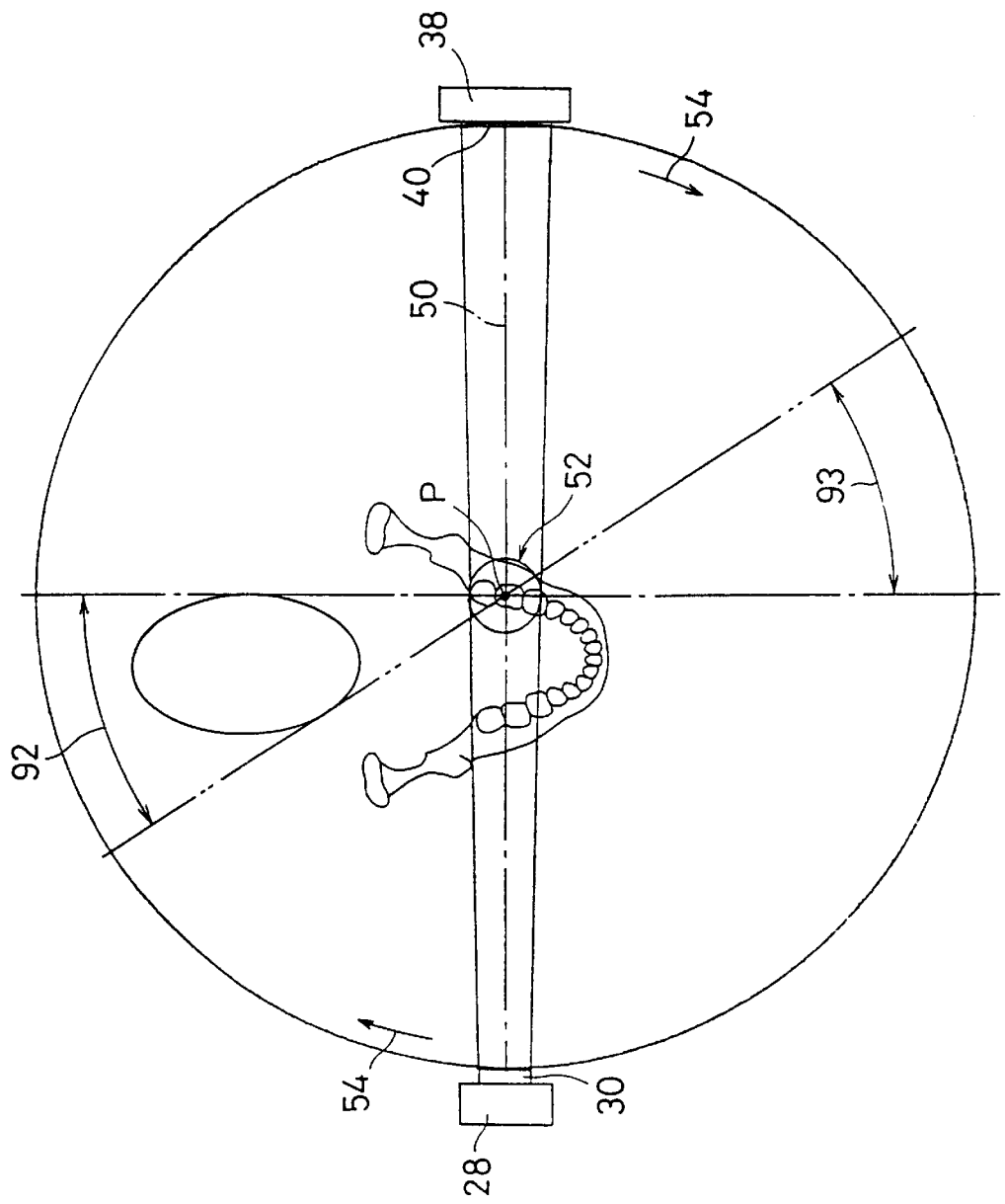

X-RAY IMAGING APPARATUS

BACKGROUND OF THE INVENTION

1. Field of the Invention

The present invention relates to an X-ray imaging apparatus which takes an image of an object such as the jaw and facial area, tooth area and otolaryngologic area of a human body, along a desired tomographic plane.

2. Description of the Related Art

In the field of medical X-ray diagnosis, there is well known an X-ray CT (computed tomography) apparatus which takes a CT image of an arbitrary site of a human body. In such an X-ray CT apparatus, an X-ray source and X-ray imaging means opposed to the X-ray source are revolved by 360° around an object of an arbitrary site such as the head or trunk to obtain image information, which is processed by a computer to obtain a CT image which is a section view of the arbitrary site. Such an X-ray CT apparatus of the prior art is bulky and expensive, and hence inadequate for use in the areas of dentistry and otolaryngology.

In dental treatment, if the thickness and structure of the jaw are known prior to an implant operation or the like, the operation can be easily performed. In order to obtain such data, a miniature X-ray CT apparatus capable of obtaining X-ray CT images of a specific tooth and a vicinity thereof has been contemplated. Such a miniature X-ray CT apparatus comprises: an X-ray source for generating X-rays; X-ray imaging means for detecting X-rays which passed through an object; supporting means for supporting the X-ray source and X-ray imaging means so that they are opposed to each other across the object; and a driving source for moving the supporting means in a predetermined direction. When an X-ray CT imaging process is to be performed, the supporting means is revolved by 360° around the object by the function of the driving source. During the 360° revolution, X-rays which are emitted from the X-ray source and pass through the object enter the imaging means, and X-ray imaging is performed at predetermined angles. In such an X-ray CT apparatus, image information obtained in X-ray imaging at predetermined angles is stored in storing means, and the stored image information is subjected to CT image processing by a computer, thereby obtaining a desired CT image.

In an X-ray CT apparatus, images obtained as results of X-ray imaging at predetermined angles are subjected to the CT image processing. In the CT image processing, when an obstacle such as a metal prosthesis or a large bone structure exists in even one of the images obtained by the X-ray imaging, a clear CT image is hardly obtained by the computer processing because such obstacle absorbs a large amount of X-rays. In the case where an X-ray CT apparatus is used in the field of dental treatment, for example, a 360° imaging process is conducted on the head of the human body. In a specific range of the imaging process, X-rays from an X-ray source pass through the vertebrae cervicales and then reach X-ray imaging means, and in the other range of the imaging process, X-rays from the X-ray source reach the X-ray imaging means without passing through the vertebrae cervicales. Usually the vertebrae cervicales easily absorbs X-rays. In the specific range a smaller amount of X-rays reach the X-ray imaging means because X-rays emitted from the X-ray source pass through the vertebrae cervicales, and hence a resulting X-ray image is relatively dark. To the contrary, in the other range of the imaging process X-rays emitted from the X-ray source do not pass through the vertebrae cervicales, so that a larger amount of X-rays reach the X-ray imaging means. Therefore, a resulting X-ray image is relatively bright.

Accordingly, when an X-ray CT apparatus is used in the field of dental treatment, the density of a resulting X-ray image changes depending on the angle of imaging at which the process of imaging the object is performed. When the degree of the change is considerably large, a satisfactory CT image can not be obtained in the subsequent CT image processing using a computer.

Such a problem exists not only in an X-ray CT apparatus, but also in a panoramic X-ray imaging apparatus which takes an image of the dental arch, and a linear X-ray imaging apparatus which takes only an image of a specific tomographic plane.

SUMMARY OF THE INVENTION

It is hence an object of the invention to provide an X-ray imaging apparatus capable of obtaining a good X-ray image even when the angle of imaging is changed.

In a first aspect of the invention an X-ray imaging apparatus comprises:

an X-ray source for generating X-rays;

X-ray imaging means for detecting X-rays having passed through an object and outputting an image signal;

supporting means for supporting the X-ray source and the X-ray imaging means so that the X-ray source and the X-ray imaging means are opposed to each other across the object;

a driving source for moving the supporting means in a predetermined direction;

imaging sensitivity adjusting means for adjusting the X-ray imaging means in imaging sensitivity; and controlling means for controlling the imaging sensitivity adjusting means on the basis of the image signal outputted from the X-ray imaging means.

According to the first aspect of the invention, the controlling means controls the imaging sensitivity adjusting means in accordance with the image signal from the X-ray imaging means. When the density of a detected image is low, therefore, the imaging sensitivity of the X-ray imaging means is raised by the imaging sensitivity adjusting means. By contrast, when the density of a detected image is high, the imaging sensitivity of the X-ray imaging means is lowered by the imaging sensitivity adjusting means. In this way, the density of an image obtained by the X-ray imaging means is automatically adjusted with the result that an excellent X-ray image is obtained. The image density is adjusted not by dedicated X-ray detecting means, but using the image signal from the X-ray imaging means for obtaining an X-ray image. Therefore, the adjustment of the image density can be conducted by a relatively simple configuration and on the basis of an obtained X-ray image.

In a second aspect of the invention, the X-ray source is composed of an X-ray tube which is provided with X-ray tube current adjusting means for adjusting a current supplied to the X-ray tube and/or X-ray tube voltage adjusting means for adjusting a voltage applied to the X-ray tube, and the controlling means controls first the imaging sensitivity adjusting means on the basis of the image signal from the X-ray imaging means and controls the X-ray tube current adjusting means and/or the X-ray tube voltage adjusting means when the image signal is out of an adjustment range of the imaging sensitivity adjusting means.

According to the second aspect of the invention, the X-ray tube current adjusting means and/or the X-ray tube voltage adjusting means is provided, and these means are controlled by the controlling means. The control by the controlling means is performed in the following manner. First, the imaging sensitivity adjusting means adjusts the imaging sensitivity of the X-ray imaging means. When the adjustment of the imaging sensitivity of the X-ray imaging means becomes unable to cope with the requirement, the intensity of X-rays emitted from the X-ray tube is adjusted by the X-ray tube current adjusting means and/or the X-ray tube voltage adjusting means. Therefore, the imaging sensitivity is preferentially adjusted, so that the density adjustment is conducted with high response characteristics. In addition to the adjustment of the imaging sensitivity of the X-ray imaging means, the adjustment of the voltage applied to the X-ray tube and/or that of the current supplied to the X-ray tube are conducted. Consequently, the image density can be automatically adjusted in a wider range.

In a third aspect of the invention, in relation to the driving source, driving speed adjusting means for adjusting a driving speed of the driving source is provided, which is controlled by the controlling means, and the controlling means controls first the imaging sensitivity adjusting means on the basis of the image signal from the X-ray imaging means, controls the X-ray tube current adjusting means and/or the X-ray tube voltage adjusting means when the image signal is out of a predetermined adjustment range of the imaging sensitivity adjusting means, and controls the driving speed adjusting means when the image signal is out of a combination adjustment range of the predetermined adjustment ranges of the imaging sensitivity adjusting means, and the X-ray tube current adjusting means and/or the X-ray tube voltage adjusting means.

According to the third aspect of the invention, the driving speed adjusting means for adjusting the driving speed of the driving source is provided, and the driving speed adjusting means is controlled by the controlling means. The control by means of the controlling means is performed in the following manner. First, the imaging sensitivity adjusting means adjusts the imaging sensitivity of the X-ray imaging means.

When the adjustment of the imaging sensitivity of the X-ray imaging means becomes unable to cope with the requirement, the intensity of X-rays emitted from the X-ray tube is adjusted by the X-ray tube current adjusting means and/or the X-ray tube voltage adjusting means. When the adjustment of the X-ray intensity by means of the X-ray tube current adjusting means and/or the X-ray tube voltage adjusting means becomes unable to cope with the requirement, the driving speed of the driving source is adjusted by the driving speed adjusting means. In accordance with precedence, the adjustment of the imaging sensitivity of the X-ray imaging means is first conducted, and the adjustment of the X-ray intensity of the X-ray tube is then conducted. Therefore, the automatic density adjustment is conducted in a wider range with high response characteristics. In addition to the adjustments of the imaging sensitivity of the X-ray imaging means and the X-ray intensity of the X-ray tube, the adjustment of the driving speed of the driving source is conducted. Consequently, the image density can be automatically adjusted in a further wider range.

In a fourth aspect of the invention, the X-ray imaging apparatus further comprises, in relation to the driving source, driving speed adjusting means for adjusting a driving speed of the driving source, which is controlled by the controlling means, and the controlling means controls first the imaging sensitivity adjusting means on the basis of the image signal from the X-ray imaging means, and controls the driving speed adjusting means when the image signal is out of a predetermined adjustment range of the imaging sensitivity adjusting means.

According to the fourth aspect of the invention, the driving speed adjusting means is provided, and the driving speed adjusting means is controlled by the controlling means. The control by means of the controlling means is performed in the following manner. First, the imaging sensitivity adjusting means adjusts the imaging sensitivity of the X-ray imaging means. When the adjustment of the imaging sensitivity of the X-ray imaging means becomes unable to cope with the requirement, the driving speed of the driving source is adjusted by the driving speed adjusting means. Therefore, the imaging sensitivity is preferentially adjusted, so that the density adjustment is conducted with high response characteristics. In addition to the adjustment of the imaging sensitivity of the X-ray imaging means, the adjustment of the driving speed of the driving source is conducted. Consequently, the image density can be automatically adjusted in a further wider range.

In a fifth aspect of the invention, the X-ray source is composed of an X-ray tube which is provided with X-ray tube current adjusting means for adjusting a current supplied to the X-ray tube and/or X-ray tube voltage adjusting means for adjusting a voltage applied to the X-ray tube, and the controlling means simultaneously controls the imaging sensitivity adjusting means, and the X-ray tube current adjusting means and/or the X-ray tube voltage adjusting means, on the basis of the image signal from the X-ray imaging means.

According to the fifth aspect of the invention, the X-ray source is composed of an X-ray tube, and the X-ray tube current adjusting means for adjusting a current supplied to the X-ray tube and/or the X-ray tube voltage adjusting means for adjusting a voltage applied to the X-ray tube are provided. Since the controlling means simultaneously controls the X-ray tube current adjusting means and the X-ray tube voltage adjusting means and/or the X-ray tube current adjusting means on the basis of the image signal from the X-ray imaging means, the adjustments of the image density can be simultaneously conducted in a wider range. Even when an X-ray tube of a small rating current and a low rating voltage is used, therefore, it is possible to obtain a clear image of a wide dynamic range.

In a sixth aspect of the invention, the X-ray imaging apparatus further comprises, in relation to the driving source, driving speed adjusting means for adjusting a driving speed of the driving source, and the controlling means simultaneously controls the imaging sensitivity adjusting means, the X-ray tube current adjusting means and/or the X-ray tube voltage adjusting means, and the driving speed adjusting means, on the basis of the image signal from the X-ray imaging means.

According to the sixth aspect of the invention, the driving speed adjusting means for adjusting a driving speed of the driving source is provided. Since the controlling means simultaneously controls the imaging sensitivity adjusting means, either or both of the X-ray tube current adjusting means and the X-ray tube voltage adjusting means, and the driving speed adjusting means on the basis of the image signal from the X-ray imaging means, the adjustments of the image density can be simultaneously conducted in a further wider range.

In a seventh aspect of the invention, the X-ray imaging apparatus further comprises, in relation to the driving source, driving speed adjusting means for adjusting a driving speed of the driving source, and the controlling means simultaneously controls the imaging sensitivity adjusting means and the driving speed adjusting means on the basis of the image signal from the X-ray imaging means.

According to the seventh aspect of the invention, the driving speed adjusting means for adjusting a driving speed of the driving source is provided, and the controlling means can simultaneously control the imaging sensitivity adjusting means and the driving speed adjusting means on the basis of the image signal from the X-ray imaging means. Therefore, the adjustment of the image density can be conducted in a wider range.

BRIEF DESCRIPTION OF THE DRAWINGS

Other and further objects, features, and advantages of the invention will be more explicit from the following detailed description taken with reference to the drawings wherein:

FIG. 4 is a diagram illustrating loci of an X-ray tube and an image sensor in obtaining a CT image;

DETAILED DESCRIPTION OF THE PREFERRED EMBODIMENTS

Figure 1:
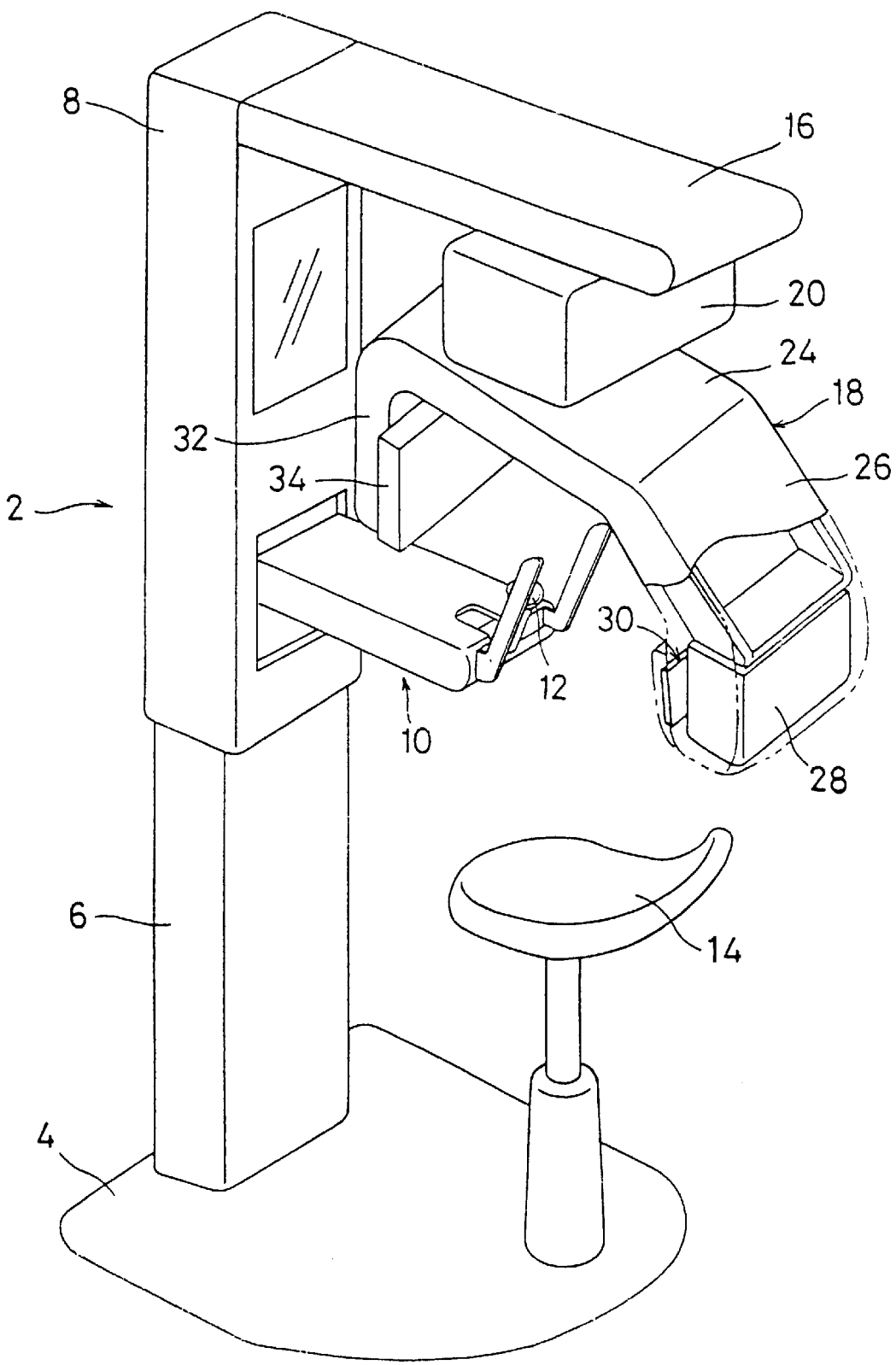
FIG. 1 is a partially cutaway perspective view showing an embodiment of an X-ray imaging apparatus of the invention.

Now referring to the drawings, preferred embodiments of the invention are described below.

Hereinafter, an embodiment of the X-ray imaging apparatus of the invention will be described with reference to the accompanying drawings. Referring to FIG. 1, an illustrated X-ray imaging apparatus comprises an apparatus frame 2. The apparatus frame 2 has a base 4 which is to be placed on a floor, and a column 6 is disposed on the base 4. The column 6 elongates from the base 4 in an upward direction which is substantially perpendicular to the base. An elevator frame 8 is mounted on the column 6 so as to be vertically movable. A chin rest 12 is mounted on the elevator frame 8 via a support position adjusting mechanism 10 so that its position is arbitrarily set. A chair 14 for patient is disposed on the base 4. The patient as an object sits in the chair 14 and the chin is positioned on the chin rest 12 so that a site to be imaged is placed in an imaging area of the X-ray imaging apparatus. Thereafter, the X-ray imaging operation is conducted on a predetermined site in the manner described later. Although not clearly illustrated, the position of the chin rest 12 can be adjusted in vertical, lateral, and anteroposterior directions by the support position adjusting mechanism 10.

A horizontal arm 16 is disposed at the upper end portion of the elevator frame 8. The horizontal arm 16 elongates in the forward direction or toward the right lower portion in FIG. 1. Supporting means 18 is mounted on the tip end portion of the arm 16. A plane moving mechanism 20 is interposed between the horizontal arm 16 and the supporting means 18. The mechanism 20 comprises an X-axis table which is movable in the anteroposterior direction (the direction from the right lower portion to the left upper portion in FIG. 1) with respect to the horizontal arm 16, and a Y-axis table which is movable in the lateral direction (the direction from the left lower portion to the right upper portion in FIG. 1) perpendicular to the anteroposterior direction. A rotation shaft 22 (see FIG. 2) is rotatably supported at the tip end portion of the plane moving mechanism 20. The supporting means 18 is mounted on the rotation shaft 22. The supporting means 18 has a support arm 24 which can extend in a predetermined direction. The center portion of the support arm 24 is attached to the rotation shaft 22. A first mounting portion 26 which can downward elongate is integrated with one end portion of the support arm 24. An X-ray tube 28 serving as the X-ray source, and primary slit means 30 are disposed on the first mounting portion 26. The primary slit means 30 is placed in proximity to and in front of the X-ray tube 28. A second mounting portion 32 which can downward elongate is integrated with the other end portion of the support arm 24. An X-ray imaging unit 34 is mounted on the second mounting portion 32. The X-ray imaging unit 34 has X-ray imaging means for detecting X-rays emitted from the X-ray tube 28. In the embodiment, the X-ray imaging means is configured by an image sensor 38 (see FIG. 2). In the X-ray imaging unit 34, secondary slit means 40 (see FIG. 2) which is opposed to the X-ray tube 28 is placed in proximity to and in front of the image sensor 38.

Figure 2:
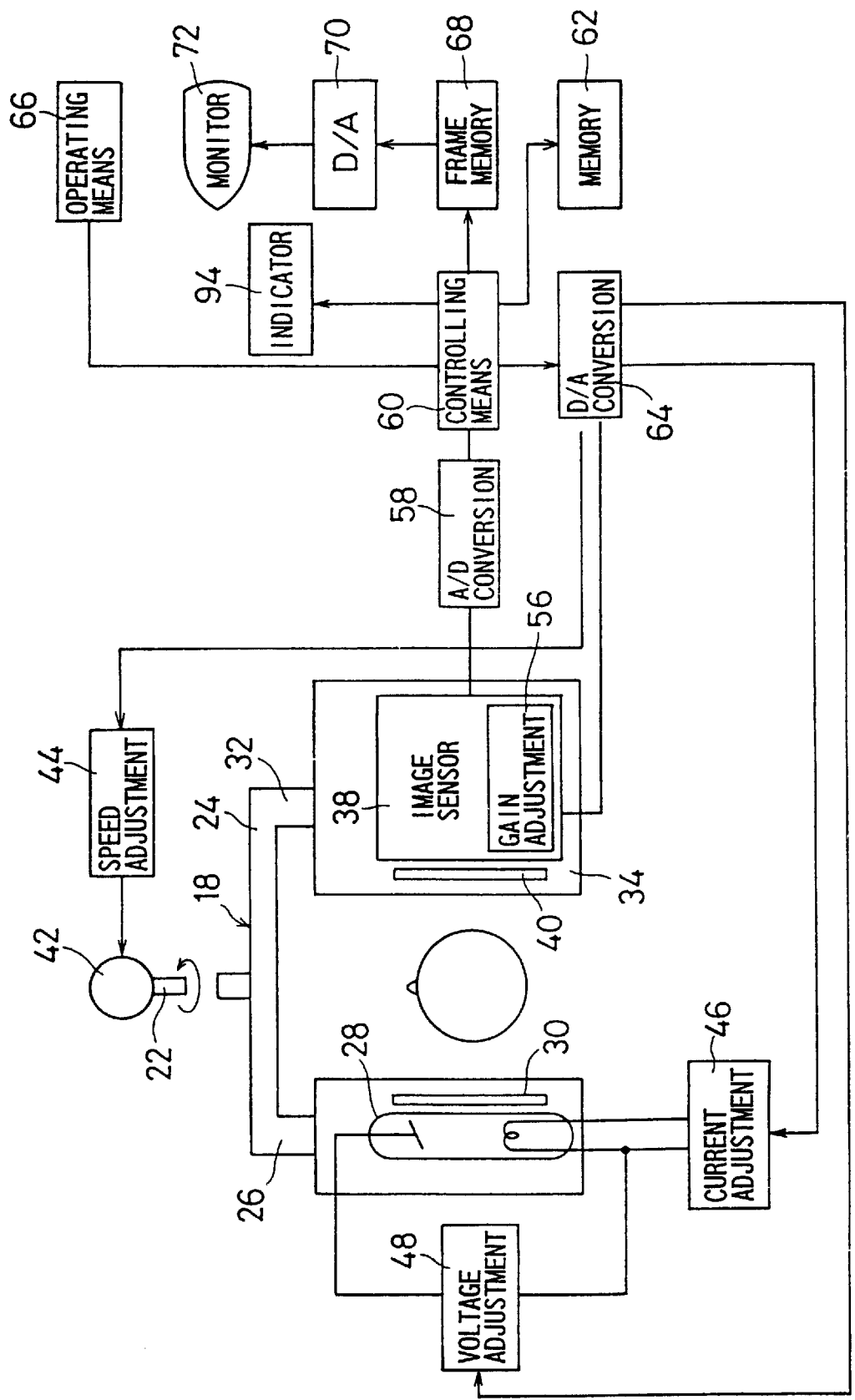
FIG. 2 is a block diagram showing an outline of the X-ray imaging apparatus of FIG. 1.

Referring to FIG. 2 together with FIG. 1, the object which is to be subjected to the X-ray imaging operation is positioned between the X-ray tube 28 and the image sensor 38. The object is irradiated with X-rays emitted from the X-ray tube 28. The primary slit means 30 restricts the width and height of X-rays emitted from the X-ray tube 28, thereby preventing unnecessary X-rays from being emitted toward the object. X-rays which pass through the object are detected by the image sensor 38. The secondary slit means 40 restricts the width and height of X-rays entering the image sensor 38, thereby preventing unnecessary X-rays from entering the image sensor 38. Preferably, the slits of the primary and secondary slit means 30 and 40 which are selected in the X-ray imaging operation are similar in shape to each other and the slit of the secondary slit means 40 is set to be slightly larger than that of the primary slit means 30. When a partial CT image is to be obtained by the X-ray imaging apparatus, the apertures of the slits of the primary and secondary slit means 30 and 40 are set to be rectangular or square.

Next, referring mainly to FIG. 2, an outline of the X-ray imaging apparatus will be described. A driving motor 42 constituting the driving source is drivingly coupled to the rotation shaft 22. The driving motor 42 is provided with driving speed adjusting means 44 for adjusting the rotation speed of the motor. For example, the driving speed adjusting means 44 is configured by a current change circuit which changes the level of a current supplied to the driving motor 42. The driving speed adjusting means 44 can adjust the rotation speed of the driving motor 42, i.e., the revolution speed of the support arm 24 which will be described later. The X-ray tube 28 is provided with X-ray tube current adjusting means 46 for adjusting a current supplied to the X-ray tube 28, and X-ray tube voltage adjusting means 48 for adjusting a voltage applied to the X-ray tube 28. For example, the X-ray tube current adjusting means 46 is configured by a current change circuit which changes the level of the current supplied to the X-ray tube 28, so that the level of the current supplied to the X-ray tube 28, i.e., the intensity of X-rays emitted from the X-ray tube 28 can be adjusted by the X-ray tube current adjusting means 46. The X-ray tube voltage adjusting means 48 is configured by a voltage change circuit which changes the level of the voltage applied to the X-ray tube 28, so that the level of the voltage applied to the X-ray tube 28, i.e., the intensity and quality of X-rays emitted from the X-ray tube 28 can be adjusted by the X-ray tube voltage adjusting means 48.

Figure 3:
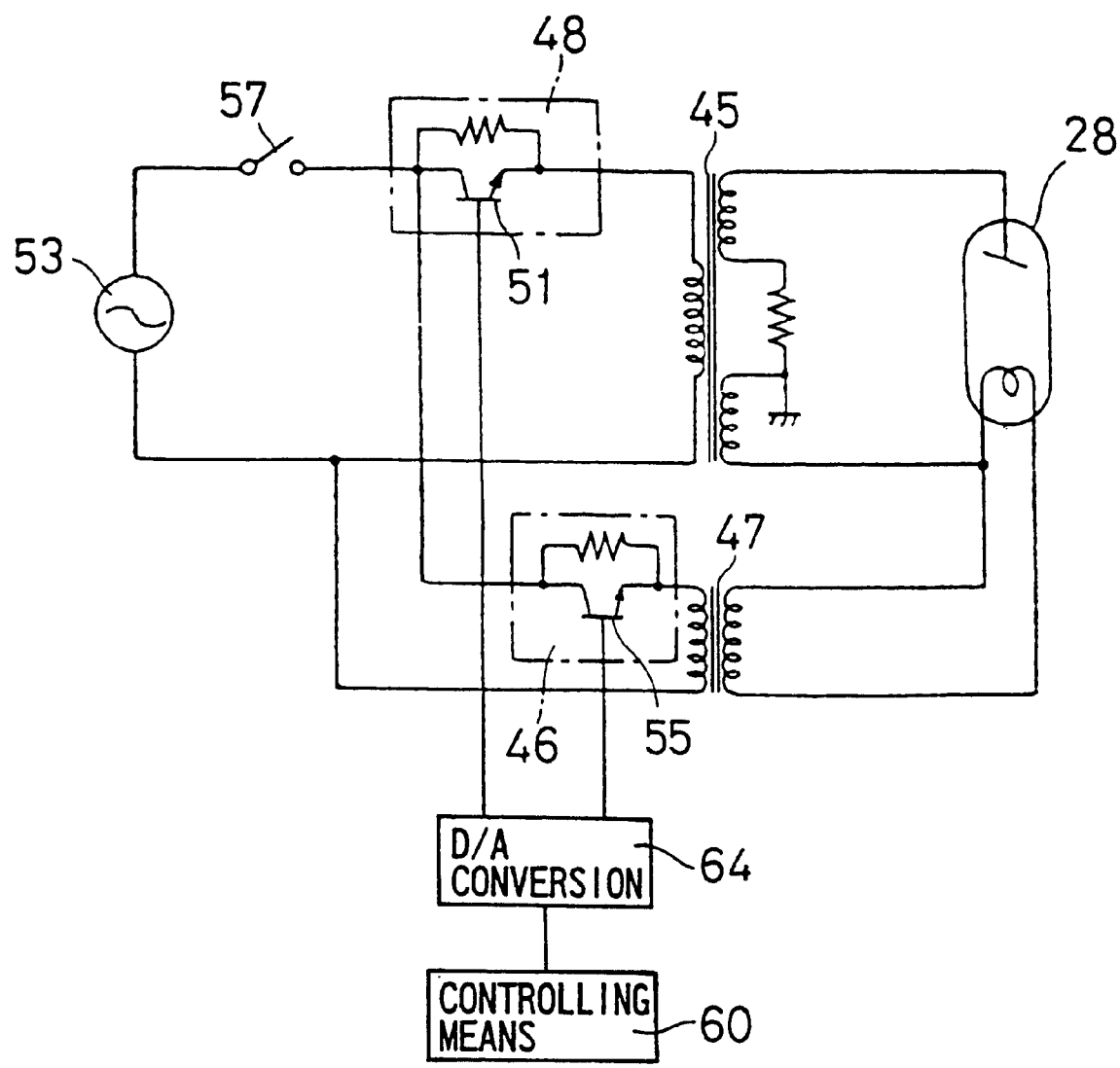
FIG. 3 is a circuit diagram showing examples of X-ray tube voltage adjusting means and X-ray tube current adjusting means in the X-ray imaging apparatus of FIG. 1.

For example, the current change circuit and the voltage change circuit may be configured as shown in FIG. 3. A high-voltage transformer 45 and a filament transformer 47 are connected to the X-ray tube 28. The primary side of the high-voltage transformer 45 is connected to an AC power source 53 via a feedback control transistor 51 constituting the X-ray tube voltage adjusting means 48. The primary side of the filament transformer 47 is connected to the AC power source 53 via a feedback control transistor 55 constituting the X-ray tube current adjusting means 46. A power source switch 57 is connected between the AC power source 53 and the feedback control transistors 51 and 55. A signal supplied from controlling means 60 to a D/A converting means 64 causes the base bias (conduction angle) of each of the feedback control transistors 51 and 55, thereby conducting a feedback control on the high-voltage transformer 45 and the filament transformer 47. The use of such circuits enables the application voltage and the filament current of the X-ray tube 28 to be changed, whereby the tube voltage and the tube current of the X-ray tube 28 can be simultaneously controlled. The control of the tube voltage and the tube current of the X-ray tube 28 is described in, for example, Japanese Examined Patent publication JP-B2 2-47839 (1990), and hence its detailed description is omitted.

When a partial CT image is to be obtained by the X-ray imaging apparatus, the X-ray tube 28 and the image sensor 38 are moved as shown in FIG. 4. Specifically, in the partial CT imaging process, a range of, for example, about 50 mm which is centered at the center point P (the center point P coincides with the center axis of the rotation shaft 22) of a line 50 connecting the X-ray tube 28 and the image sensor 38 as shown in FIG. 4 is used as an imaging area 52. During the partial CT imaging process, the center point P is not varied. The X-ray tube 28 and the image sensor 38 are integrally revolved at a predetermined rotational speed about the center point P by 360°, for example, in a clockwise direction indicated by the arrow 54. As a result of the revolution, an omnidirectional or 360° image of the site to be imaged which is positioned in the imaging area 52 is obtained. In the embodiment, since the primary slit means 30 defines the rectangular or square slit aperture, X-rays from the X-ray tube 28 impinges on the imaging area 52, in the form of a pyramid or a quad-regular pyramid. The image sensor 38 generates a signal of the corresponding image at intervals of one degree in the revolution direction indicated by the arrow 54, so that signals corresponding to 360 images are generated as a result of the revolution of 360°. When a partial CT image of a higher accuracy is to be obtained, the imaging interval is set more finely (e.g., 0.5°).

Referring again to FIG. 2, an image signal detected by the image sensor 38 is processed in the following manner. The image sensor 38 comprises a gain adjusting circuit 56 constituting the imaging sensitivity adjusting means. The image signal detected by the image sensor 38 is subjected to an adjustment of the output level by the gain adjusting circuit 56. Specifically, when the level of an image signal outputted from the image sensor 38 is low, the level is increased, and, when the level of the image signal is high, the level is reduced, so that the gain adjusting circuit 56 outputs an image signal of a level which is in a predetermined range. When the adjustment conducted by the gain adjusting circuit 56 cannot maintain the level of the image signal in the predetermined range, the level of the image signal outputted from the gain adjusting circuit 56 is adjusted by the X-ray tube current adjusting means 46 and the X-ray tube voltage adjusting means 48, and further by the driving speed adjusting means 44, as described later.

The image signal output from the gain adjusting circuit 56 of the image sensor 38 is supplied to A/D converting means 58, and then converted into a digital signal in the A/D converting means 58. The image signal which has been converted into a digital signal is supplied to the controlling means 60.

The controlling means 60 may be configured by a microprocessor or the like. In relation to the controlling means 60, memory means 62 is disposed. The memory means 62 is configured by, for example, a RAM. The image information which has undergone the digital conversion is stored together with imaging information (for example, imaging angle information) in the memory means 62. The controlling means 60 checks the digital-converted image information to see whether the image information is within an appropriate level range or not, i.e. whether the signal level of a part or the whole of the image information is higher than a first predetermined level which is close to saturation or lower than a second predetermined level at which the signal is hardly detected. If the signal level is higher than the first predetermined level (or lower than the second predetermined level), the controlling means 60 generates a density adjust signal for increasing (or reducing) the density of the image. The density adjust signal is supplied to the D/A converting means 64. The D/A converting means 64 converts the density adjust signal into an analog signal. The analog-converted density adjust signal is supplied to the gain adjusting circuit 56, the X-ray tube current adjusting means 46, the X-ray tube voltage adjusting means 48, or the driving speed adjusting means 44, as described later.

In this way, an X-ray image of the 360° range is stored in the memory means 62.

After the X-ray imaging operation, operating means 66 is operated in order to obtain a partial CT image. Then, the image information stored in the memory means 62 is read out, and the controlling means 60 performs CT image processing on the read out image information. As a result of the image processing, a CT image is obtained. The obtained CT image is supplied to a frame memory device 68. The output of the frame memory device is converted into an analog signal by D/A converting means 70 and then supplied to monitor means 72 which may be a display device, and which in turn displays the obtained CT image.

Preferably, a MOS image sensor may be used as the image sensor 38. Next, referring to FIG. 5, the operation principle of a MOS image sensor will be described.

Figure 5A:
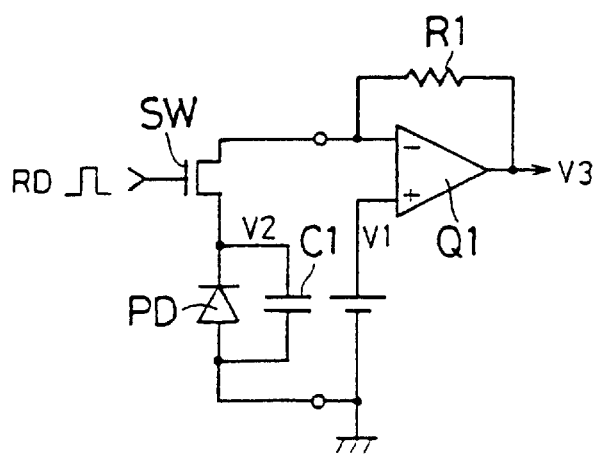
FIG. 5A is a circuit diagram illustrating an operation principle of a MOS sensor used in the X-ray imaging apparatus of FIG. 1.

Referring to FIG. 5A, a photodiode PD constituting a light receiving pixel converts entering light into an electric signal. A switch SW configured by a MOSFET is connected in series to the photodiode PD. The switch is connected also to the inverting terminal of an operational amplifier Q1. A feedback resistor R1 is connected to the operational amplifier Q1 so as to constitute a current/voltage converting circuit, whereby an input current is output as a voltage signal. A voltage V1 with respect to the ground (GND) is applied to the noninverting terminal of the operational amplifier Q1.

Figure 5B:
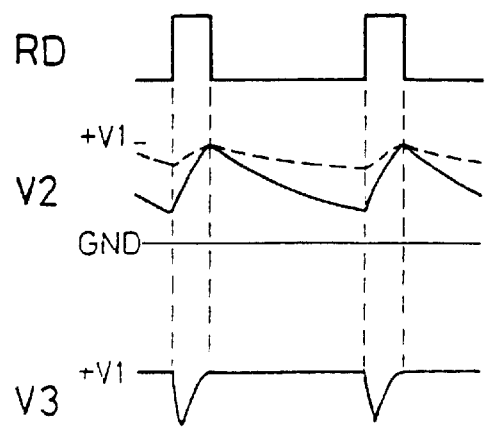
FIG. 5B is a chart showing operation timing of the MOS sensor.

Referring to FIG. 5B, when a positive read pulse RD is supplied to the gate of the switch SW, the switch SW is opened and the photodiode PD is inversely biased so that the junction capacity C1 is charged by a predetermined amount of charges.

The switch SW is then closed. When light enters during an accumulation period, the charges of the capacity are caused to be discharged by charges due to the light incidence, and hence the cathode potential of the photodiode PD gradually approaches the ground potential. The amount of the discharged charges is increased in proportion to the amount of the incident light. When the read pulse RD is then supplied to the gate of the switch SW and the switch SW is opened, charges corresponding to the charges which are discharged during the accumulation period are supplied via the feedback resistor R1 and the photodiode PD is returned to the inversely biased state so as to be initialized. At this time, a potential difference is produced across the feedback resistor R1 by the charging current.

This potential difference is output from the operational amplifier Q1 as a voltage signal. The charging current corresponds to the discharge current due to the light incidence, and hence the amount of the incident light can be detected on the basis of the output voltage.

Figure 6:
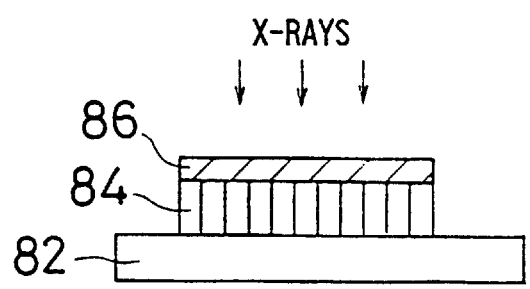
FIG. 6 is a section view showing the structure of the MOS sensor in the X-ray imaging apparatus of FIG. 1.

FIG. 6 is a section view showing the configuration of the X-ray image sensor 38. Optical fiber elements (FOP) 84 through which an optical image is transmitted are disposed on a MOS image sensor 82 in which photodiodes PD are two-dimensionally arranged. A scintillator layer 86 which converts X-rays into visible light is formed on the optical fiber elements 84. The image of X-rays which pass through the object is converted into a visible light image by the scintillator layer 86. The visible light image is transmitted by the optical fiber elements 84, and then subjected as it is to the photoelectric conversion by the MOS image sensor 82.

Figure 7:
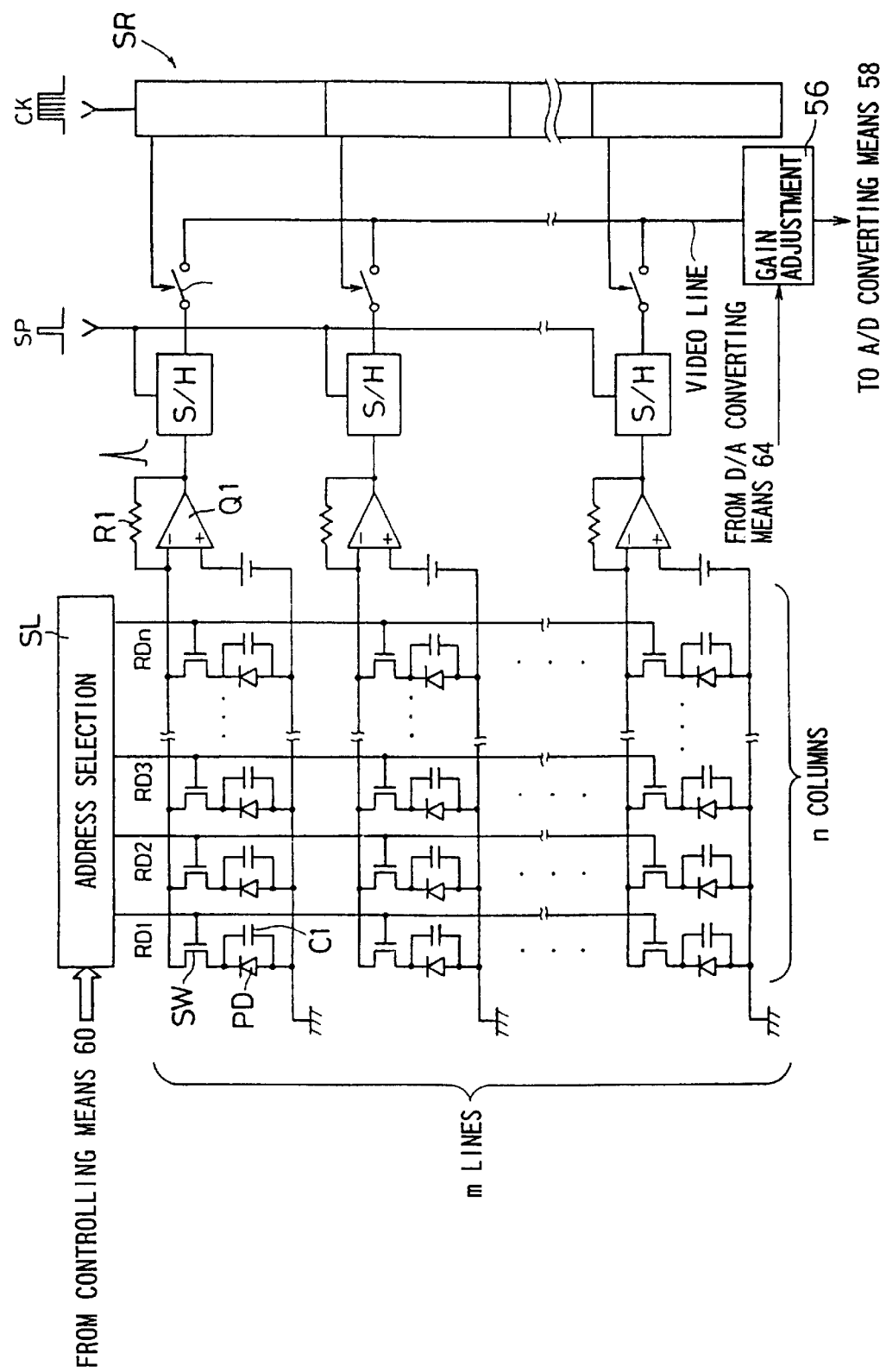
FIG. 7 is a circuit diagram showing a driving circuit for the MOS sensor in the X-ray imaging apparatus of FIG. 1.

FIG. 7 shows a driving circuit for the MOS image sensor 82. The photodiodes PD serving as light receiving pixels are arranged into a matrix of m lines H n columns. The junction capacity C1 is connected in parallel with each photodiode PD, and the read switch SW is connected in series to each photodiode PD. An address selection circuit SL is connected to the gates of the switches SW. The photodiode PD from which image information is to be read out is selected on the basis of a signal from the controlling means 60.

The outputs of the switches SW of each line are connected to each other and then supplied to corresponding one of operational amplifiers Q1 constituting the current/voltage converting circuit. The output of the operational amplifier Q1 is sampled by a sample and hold (S/H) circuit. Each sample and hold circuit is connected to a switch SWb which is closed and opened by an m-stage shift register SR. The switches SWb are sequentially closed and opened, so that the sampled signals are supplied as a time-series signal to the controlling means 60 via the gain adjusting circuit 56 and the A/D converting means 58.

Figure 8:
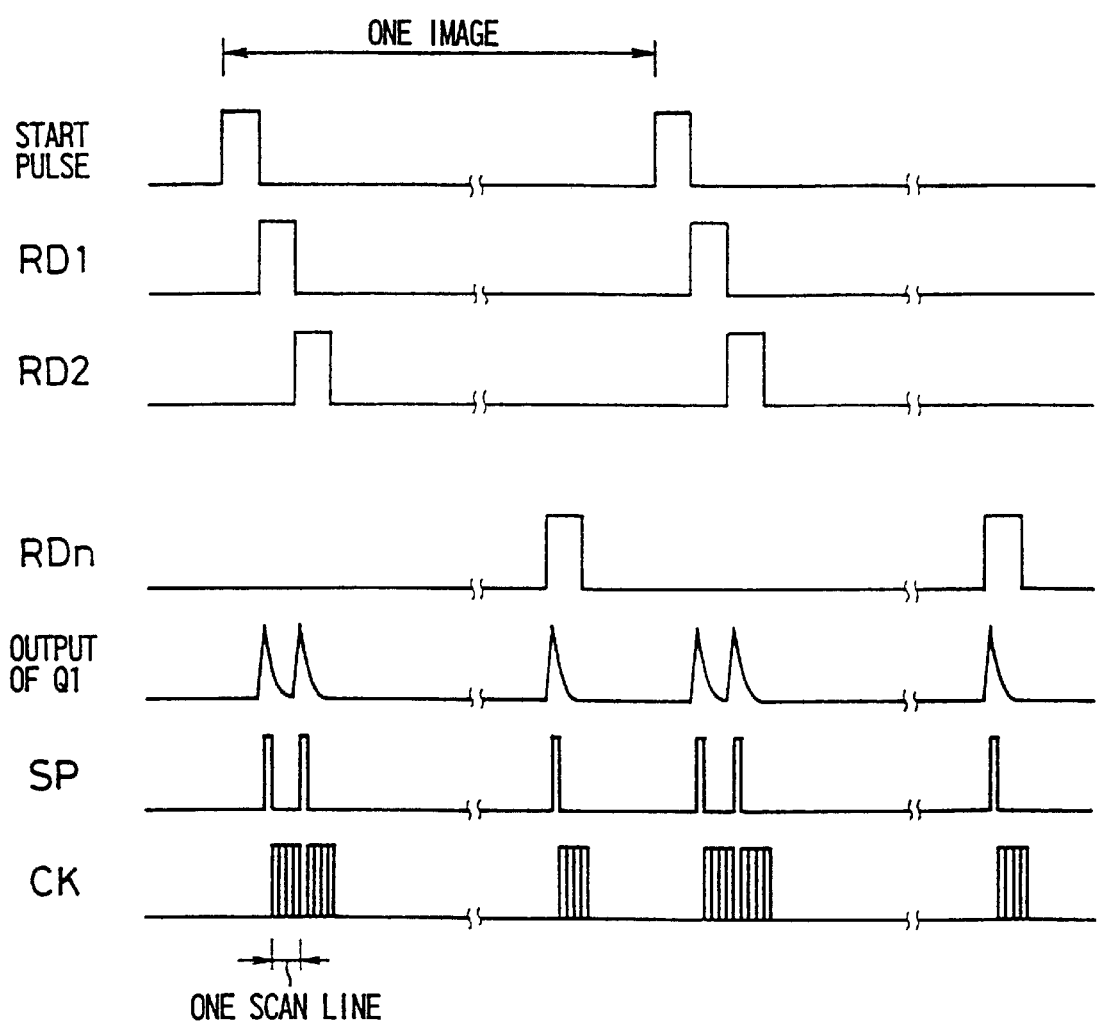
FIG. 8 is a timing chart illustrating the operation of the MOS sensor driving circuit of FIG. 7.

FIG. 8 is a timing chart illustrating the operation of the driving circuit of FIG. 7. Hereinafter, an example in which a shift register is used as the address selection circuit SL will be described. The address selection circuit SL is activated by a start pulse supplied from the controlling means 60, and outputs in sequence a first-column read pulse RD1, a second-column read pulse RD2, ), an nth-column read pulse RDn in synchronization with a read clock pulse signal supplied from the controlling means 60.

When the first-column read pulse RD1 is supplied to the gates of the switches SW of the first column, for example, charges corresponding to the amount of the incident light of the photodiodes PD of the first column are read out, and the operational amplifiers Q1 output voltage signals. A sampling pulse SP is supplied to the sample and hold circuits so as to sample the output of the operational amplifier Q1 at the timing of a peak value. The sampled signals are supplied to the shift register SR, and transferred by a shift clock signal CK consisting of m pulses until the next sampling pulse SP is supplied, so as to be output as an image signal for one scan line. Also for the second and subsequent columns, in the same manner as described above, signals for m lines are read out in parallel by one read pulse and a time series signal for one scan line is configured by the shift register SR. Such MOS image sensors may be electrically connected to each other so as to configure two, or three or more stages.

Figure 9:
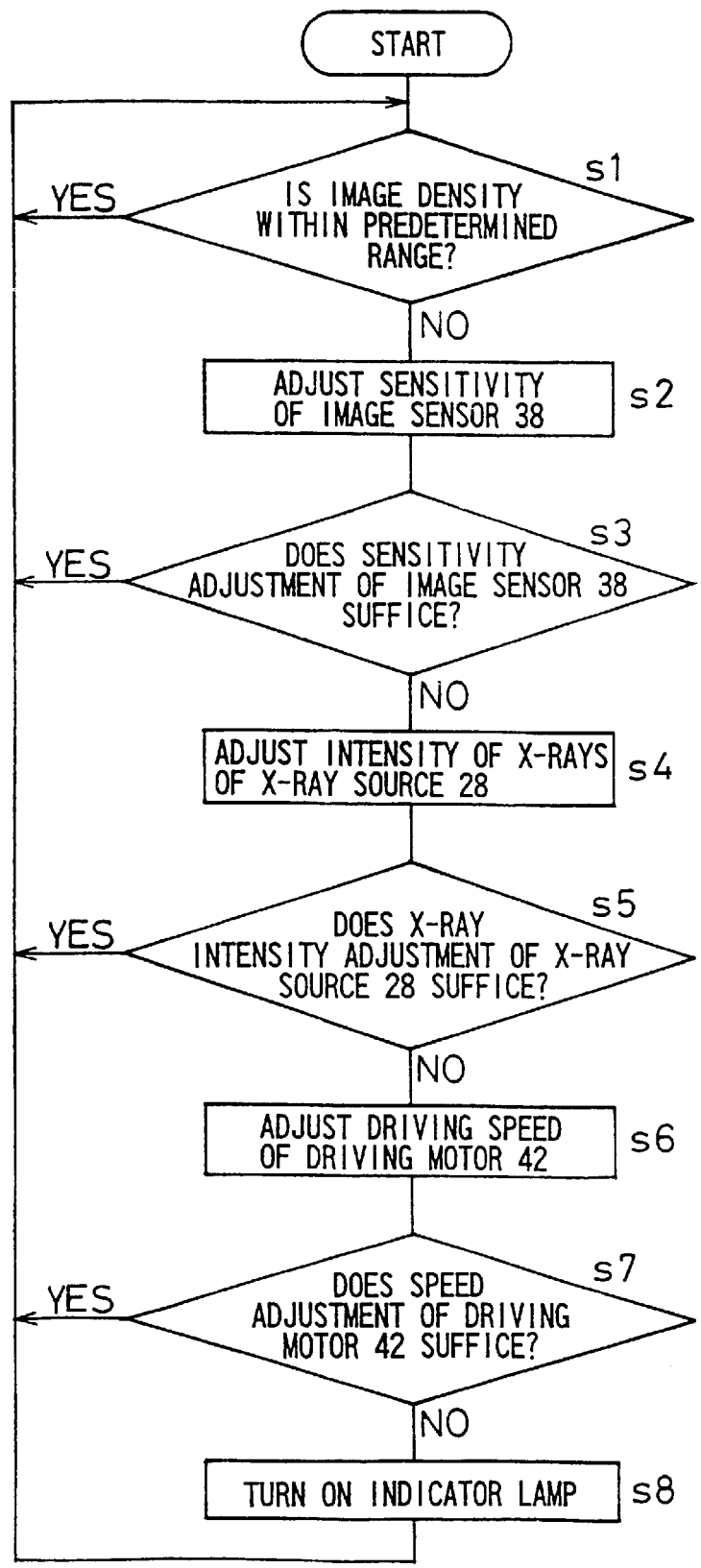
FIG. 9 is a flowchart illustrating the operation of an image density adjustment in the X-ray imaging apparatus of FIG. 1.

Next, referring mainly to FIGS. 2, 4, and 9, the operation of the image density adjustment conducted by the controlling means 60 will be described. During the X-ray imaging process, the image density is adjusted in accordance with a flowchart shown in FIG. 9. In step S1, the image signal from the image sensor 38 is supplied to the controlling means 60 via the A/D converting means 58. In the controlling means 60, it is judged whether the level of the image signal is within the predetermined range or not. If the image signal is within the predetermined range, i.e., the signal level of a part or the whole of the image information detected by the image sensor 38 is lower than the first predetermined level which is close to saturation and higher than the second predetermined level which is so low that it is difficult to detect the signal, the image information can be adequately detected. Therefore, it is not required to adjust the image density and hence the control returns to step S1.

When the X-ray tube 28 is revolved from the position shown in FIG. 4 in the direction indicated by the arrow 54 to reach an angle region 92 (or 93), for example, X-rays which are emitted from the X-ray tube 28 toward the imaging area 52 (or X-rays which are emitted from the X-ray tube 28 toward the imaging area 52 and enter the image sensor 38) are absorbed by the vertebrae cervicales 94, and hence the amount of X-rays entering the image sensor 38 is reduced and the level of the image signal from the image sensor 38 is lowered. When the image density of the image sensor 38 is lowered and the signal level of a part or the whole of the image information is lower than the second predetermined level in this way, the control proceeds from step S1 to step S2. In step S2, the controlling means 60 reduces the image density. In other words, the controlling means 60 generates an image adjust signal for brightening the image, and the image adjust signal is converted into a digital signal by the D/A converting means 64 and then supplied to the gain adjusting circuit 56. When the image adjust signal is supplied, the gain of the gain adjusting circuit 56 of the image sensor 38 is increased and the level of the image signal supplied from the image sensor 38 is raised.

As a result, the level of the signal output from the gain adjusting circuit 56 is automatically adjusted to the predetermined range in which an appropriate image can be obtained.

When the imaging sensitivity of the image sensor 38 is adjusted in this way, the control then proceeds to step S3.

In step S3, it is judged whether the imaging sensitivity adjustment of the image sensor 38 has sufficiently coped with the required adjustment or not. If the imaging sensitivity adjustment of the image sensor 38 has sufficiently coped with the requirement, the control returns from step S3 to step S1.

By contrast, when the X-ray tube 28 further moves in the angle region 92 (or 93) toward the center portion of the region and X-rays emitted from the X-ray tube 28 are further absorbed by the vertebrae cervicales 94, the gain adjustment of the gain adjusting circuit 56 cannot sufficiently conduct the image density correction, with the result that the level of the signal supplied from the gain adjusting circuit 56 to the controlling means 60 becomes lower than the second predetermined level in spite of the adjustment conducted by the gain adjusting circuit 56. When the level is lowered in this way, the control proceeds from step S3 to step S4 in which the controlling means 60 generates an image adjust signal for reducing the image density and the image adjust signal is converted into a digital signal by the D/A converting means 64 and then supplied to the X-ray tube current adjusting means 46 and the X-ray tube voltage adjusting means 48. The supply of the image adjust signal causes the level of the current supplied to the X-ray tube 28 to be increased, and that of the voltage applied to the X-ray tube 28 to be raised, so that the intensity of X-rays emitted from the X-ray tube 28 is increased, thereby increasing the amount of X-rays entering the image sensor 38. As a result, the level of the image signal supplied from the image sensor 38 to the controlling means 60 is raised and the level of the signal output from the gain adjusting circuit 56 is automatically adjusted to the predetermined range in which an appropriate image can be obtained.

When the intensity of X-rays emitted from the X-ray tube 28 is adjusted in this way, the control then proceeds to step S5. In step S5, it is judged whether the adjustment of the X-ray intensity in step S4 has sufficiently coped with the required adjustment or not. If the above-described X-ray intensity adjustment has sufficiently coped with the requirement, the control returns from step S5 to step S1. By contrast, when the X-ray tube 28 further moves in the angle region 92 (or 93) toward the vicinity of the center portion of the region and most of X-rays emitted from the X-ray tube 28 are absorbed by the vertebrae cervicales 94, the gain adjustment by means of the gain adjusting circuit 56 and the X-ray intensity adjustment by means of the X-ray tube current adjusting means 46 and the X-ray tube voltage adjusting means 48 cannot sufficiently conduct the image density correction, with the result that the level of the signal supplied from the gain adjusting circuit 56 to the controlling means 60 becomes lower than the second predetermined level in spite of the adjustments conducted by the gain adjusting circuit 56, the X-ray tube current adjusting means 46, and the X-ray tube voltage adjusting means 48. When the level is lowered in this way, the control proceeds from step S5 to step S6 in which the controlling means 60 again generates the image adjust signal for reducing the image density and the image adjust signal is converted into a digital signal by the D/A converting means 64 and then supplied to the driving speed adjusting means 44. The supply of the image adjust signal causes the level of the current supplied from the driving speed adjusting means 44 to the driving motor 42, to be reduced, so that the rotation speed of the driving motor 42, i.e., the revolution speeds of the X-ray tube 28 and the image sensor 38 are reduced, thereby increasing the amount of X-rays entering the image sensor 38. As a result, the level of the image signal supplied from the image sensor 38 is raised and the level of the signal output from the gain adjusting circuit 56 is automatically adjusted to the predetermined range in which an appropriate image can be obtained.

When the rotation speed of the driving motor 42 is adjusted in this way, the control then proceeds to step S7.

In step S7, it is judged whether the adjustment of the rotation speed of the driving motor 42 in step S6 has sufficiently coped with the required adjustment or not. If the above-described speed adjustment of the driving motor 42 has sufficiently coped with the requirement, the control returns from step S7 to step S1. By contrast, when an abnormality occurs, the gain adjustment by means of the gain adjusting circuit 56, the X-ray intensity adjustment by means of the X-ray tube current adjusting means 46 and the X-ray tube voltage adjusting means 48, and the driving speed adjustment by means of the driving speed adjusting means 44 cannot sufficiently conduct the image density correction, with the result that the level of the signal supplied from the gain adjusting circuit 56 to the controlling means 60 becomes lower than the second predetermined level in spite of the adjustments conducted by the gain adjusting circuit 56, the X-ray tube current adjusting means 46, the X-ray tube voltage adjusting means 48, and the driving speed adjusting means 44. In such a case, the control proceeds from step S7 to step S8 in which the controlling means 60 generates an alarm signal and the alarm signal is supplied to indicating means 97 which maybe configured by an indicator lamp. When the alarm signal is supplied, the lamp is lit so that the operator is informed of a possibility that images produced by the image sensor 38 include an inadequate one.

In this way, the density of an image obtained from the image sensor 38 can be automatically adjusted. This adjusting operation is conducted in the descending order of response characteristic, i.e., in the sequence of the adjustment of the imaging sensitivity of the image sensor 38 by means of the gain adjusting circuit 56, that of the intensity of X-rays emitted from the X-ray tube 28 by means of the X-ray tube current adjusting means 46 and the X-ray tube voltage adjusting means 48, and that of the speed of the driving motor 42 by means of the driving speed adjusting means 44. Therefore, the image density adjustment can be conducted with high response characteristics, and the density adjustment can be conducted in a wider range.

In the above, the case where the amount of X-rays entering the image sensor 38 is reduced as a result of the revolution of the X-ray tube 28 and the image sensor 38 in the direction indicated by the arrow 54 has been described. In the opposite case where the amount of X-rays entering the image sensor 38 is increased (where the X-ray tube 28 passes the substantially center portion of the angle region 92 or 93 and further moves in the direction indicated by the arrow 54, the amount of X-rays absorbed by the vertebrae cervicales 94 is reduced), the image density is adjusted in a substantially same manner as described above except that the level of the image signal supplied from the image sensor 38 to the controlling means 60 is lowered. Specifically, when the level of the image signal supplied from the image sensor 38 to the controlling means 60 exceeds the first predetermined level, the signal level is lowered by the gain adjusting circuit 56, whereby the density adjustment is conducted so as to reduce the image density. When the gain adjustment by means of the gain adjusting circuit 56 cannot sufficiently cope with the requirement, the level of the current supplied to the X-ray tube 28 and that of the voltage applied to the X-ray tube are lowered by the X-ray tube current adjusting means 46 and the X-ray tube voltage adjusting means 48, thereby reducing the intensity of X-rays emitted from the X-ray tube 28. When the adjustments conducted by the X-ray tube current adjusting means 46 and the X-ray tube voltage adjusting means 48 cannot sufficiently cope with the requirement, the level of the current supplied to the driving motor 42 is raised by the driving speed adjusting means 44, so that the rotation speed of the driving motor 42, i.e., the revolution speeds of the X-ray tube 28 and the image sensor 38 are increased, thereby reducing the amount of X-rays entering the image sensor 38.

In the above, an embodiment of the X-ray imaging apparatus of the invention has been described. The invention is not restricted to such an embodiment and may be modified or changed in various manners without departing from the scope of the invention.

In the embodiment, on the basis of the image signal from the image sensor 38, the adjustment of the image density is conducted in three stages, i.e., the adjustment of the sensitivity of the image sensor 38, that of the intensity of X-rays of the X-ray tube 28, and that of the driving speed of the driving motor 42. In the case where one or two of these adjustments can sufficiently cope with the requirement, the adjustment of the image density may be conducted by any one of: the adjustment of the sensitivity of the image sensor 38; a combination of the adjustment of the imaging sensitivity of the image sensor 38 and that of the intensity of X-rays of the X-ray tube 28; or a combination of the adjustment of the imaging sensitivity of the image sensor 38 and the driving speed adjustment of the driving speed adjusting means 44.

In the embodiment, the adjustment of the sensitivity of the image sensor 38, that of the intensity of X-rays of the X-ray tube 28, and that of the driving speed of the driving motor are conducted in accordance with this order of precedence.

Alternatively, two or three of the adjustments may be simultaneously conducted. Specifically, on the basis of the image signal from the image sensor 38, the adjustment of the imaging sensitivity of the image sensor 38, and that of the intensity of X-rays of the X-ray tube 28 (the adjustments of the tube voltage and the tube current of the X-ray tube) may be simultaneously conducted; the adjustment of the imaging sensitivity of the image sensor 38, and the driving speed adjustment of the driving speed adjusting means 44 may be simultaneously conducted; or the adjustment of the imaging sensitivity of the image sensor 38, that of the intensity of X-rays of the X-ray tube, and the driving speed adjustment of the driving speed adjusting means 44 may be simultaneously conducted. As a result of such simultaneous control, the adjustment range of the image density is widened, and it is possible to obtain a clear image even when the X-ray tube 28 of a low rating voltage or a small rating current is used.

In the embodiment, the intensity of X-rays of the X-ray tube 28 is adjusted by the X-ray tube current adjusting means 46 for adjusting the current supplied to the X-ray tube 28, and the X-ray tube voltage adjusting means 48 for adjusting the voltage applied to the X-ray tube 28. In place of the adjustment conducted by the two means, the adjustment may be conducted by one of the X-ray tube current adjusting means 46 and the X-ray tube voltage adjusting means 48.

In the case where the circuit shown in FIG. 7 is used as the driving circuit for the image sensor 38, it is preferable to insert an integration circuit between the operational amplifier Q1 and the sample and hold circuit S/H. The integration circuit integrates the current (or the voltage) and the sample and hold circuit S/H samples the integrated amount. The insertion of the integration circuit causes the sampled amount to contain an integration time. As a result, the sensitivity of the image signal can be enhanced.

In the embodiment, a MOS sensor is used as the image sensor 38. In place of a MOS sensor, an image sensor of another kind such as a CCD sensor, an X.I.I. (X-ray Image Intensifier), an X.I. CCD camera (X-ray Intensified CCD camera), an X-ray solid state device consisting of thin film field effect transistors (FETs) or the like, or an X-ray semiconductor imaging device may be used.

In the above, the embodiment in which the invention is applied to an X-ray imaging apparatus for obtaining a CT image has been described. The invention may be similarly applied also to another apparatus such as an X-ray imaging apparatus which obtains a panoramic tomographic image and/or a linear tomographic image.

Figure 10:
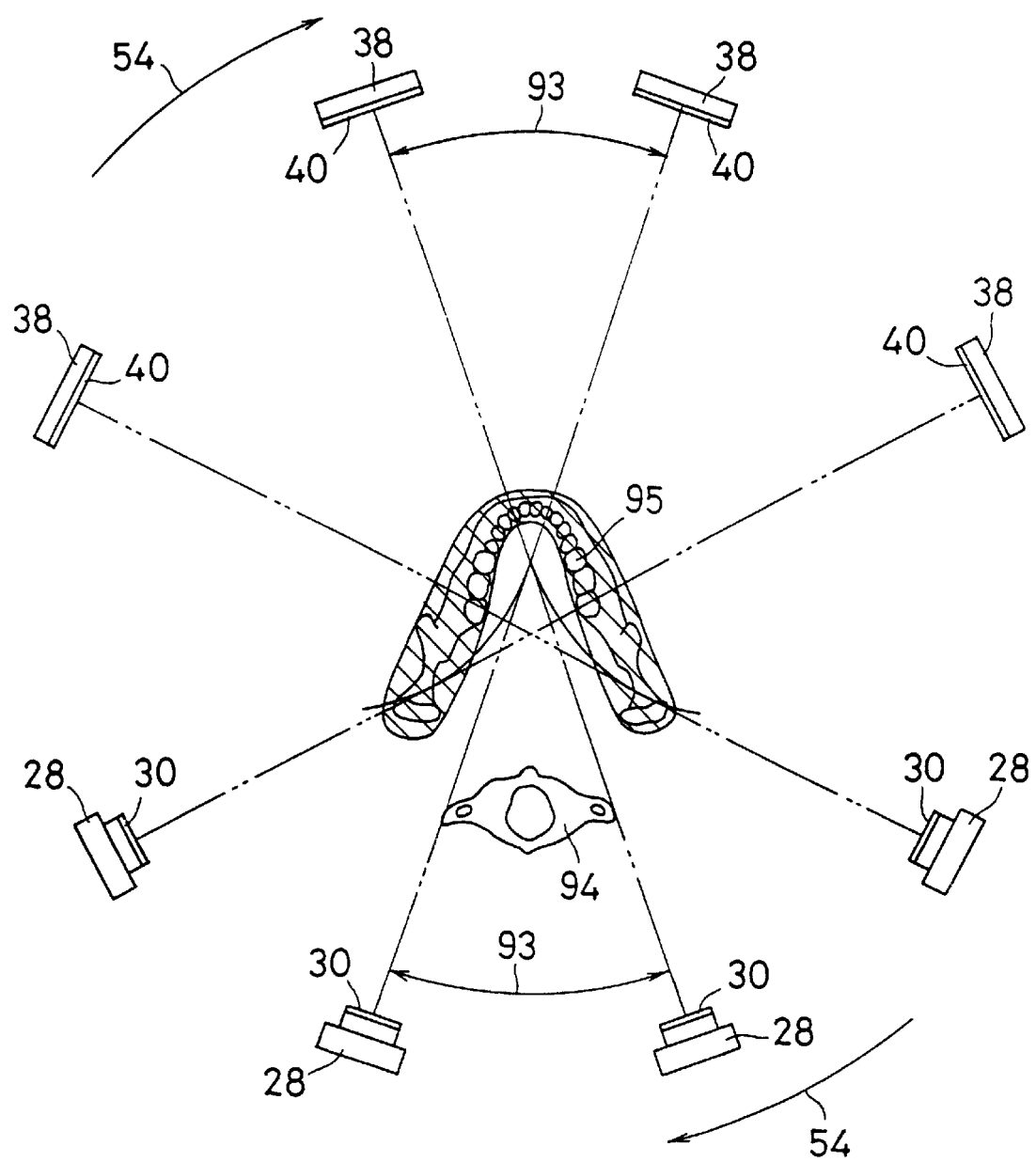
FIG. 10 is a schematic diagram illustrating loci of an X-ray tube and an image sensor in an X-ray panoramic tomography apparatus which is another example of the X-ray imaging apparatus of the invention.

FIG. 10 shows an example in which the invention is applied to an apparatus for conducting a dental panoramic tomographic X-ray imaging operation.

In the dental panoramic tomographic X-ray imaging apparatus, the X-ray tube 28 and the image sensor 38 which are disposed on supporting means and which are kept to be opposed to each other while the X-ray imaging process are revolved along the dental arch 95 of the object in the direction indicated by the arrow 54, and the instantaneous revolution center is moved in a predetermined manner, thereby obtaining an X-ray tomographic image of a curved plane including the dental arch 95 in the hatched region. In the dental panoramic tomographic X-ray imaging process, the revolution of the supporting means is conducted by the movement of the driving motor 42, and the planar movement of the supporting means is conducted by driving motors which are not shown and which respectively move the X- and Y-axis tables (not shown) of the plane moving mechanism 20 (see FIG. 2). The above-mentioned movement is realized by simultaneously driving these motors.

Also in the panoramic tomographic X-ray imaging process, in the same manner as the X-ray CT apparatus described above, the image signal from the image sensor 38 is reduced in level in the imaging region 93 where the vertebrae cervicales 94 exist.

Therefore, the image density can be adjusted by performing controls in the same manner as the X-ray CT apparatus described above.

Figure 11:
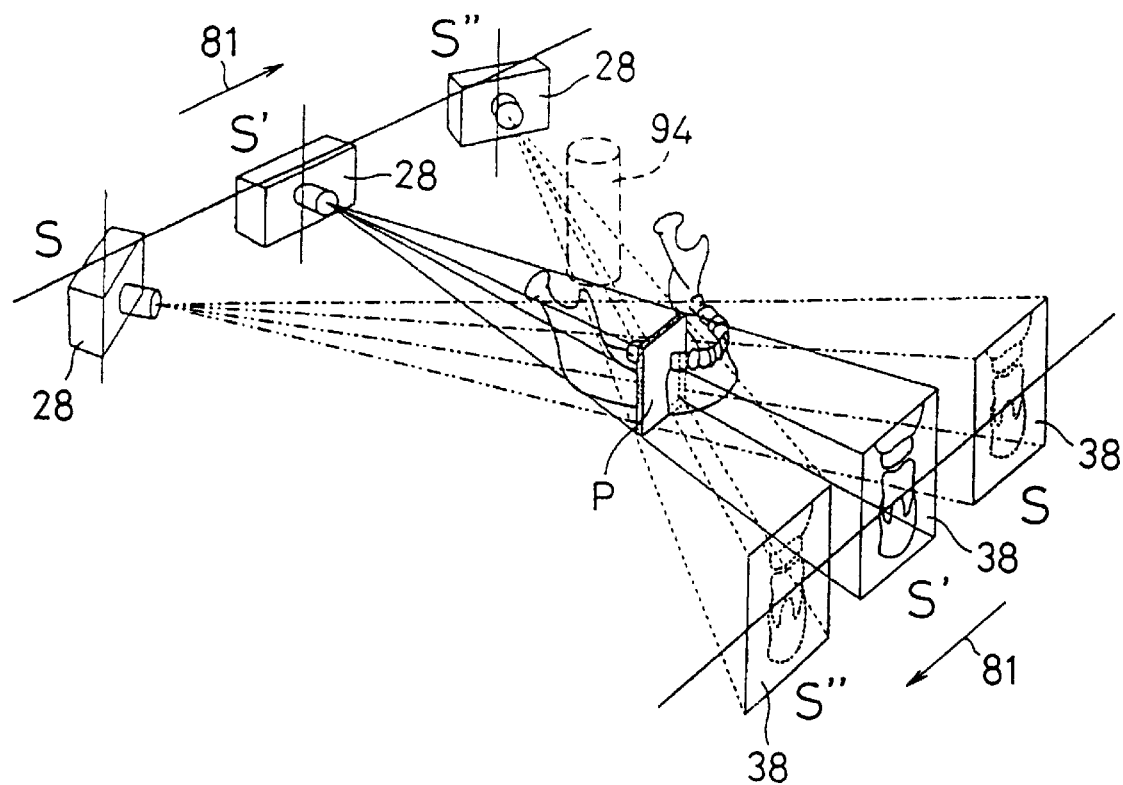
FIG. 11 is a diagram illustrating loci of an X-ray tube and an image sensor in a linear X-ray imaging apparatus which is another example of the X-ray imaging apparatus of the invention.

FIG. 11 shows an example in which the invention is applied to a dental linear X-ray imaging apparatus. In the dental linear X-ray imaging apparatus, the combination of the X-ray tube 28 and the image sensor 38 takes an image of a plane P at a desired position of the object. In the imaging process, the X-ray tube 28 and the image sensor 38 are moved in opposite directions as indicated by the arrows 81 while maintaining their parallel state with respect to the plane P. During this movement, the X-ray tube 28 is revolved with respect to the supporting means in a desired manner so that X-rays emitted from the X-ray tube 28 pass through the plane P.

In the linear X-ray imaging apparatus, the driving motor 42 (see FIG. 2) which rotates the supporting means is used only for positioning before the X-ray imaging process. The driving motor of the driving means in the invention is configured by a motor which is not shown and which moves the X-ray tube 28 and the image sensor 38 in the directions of the arrows 81 and rotate the X-ray tube 28 with respect to the supporting means.

Figure 12:
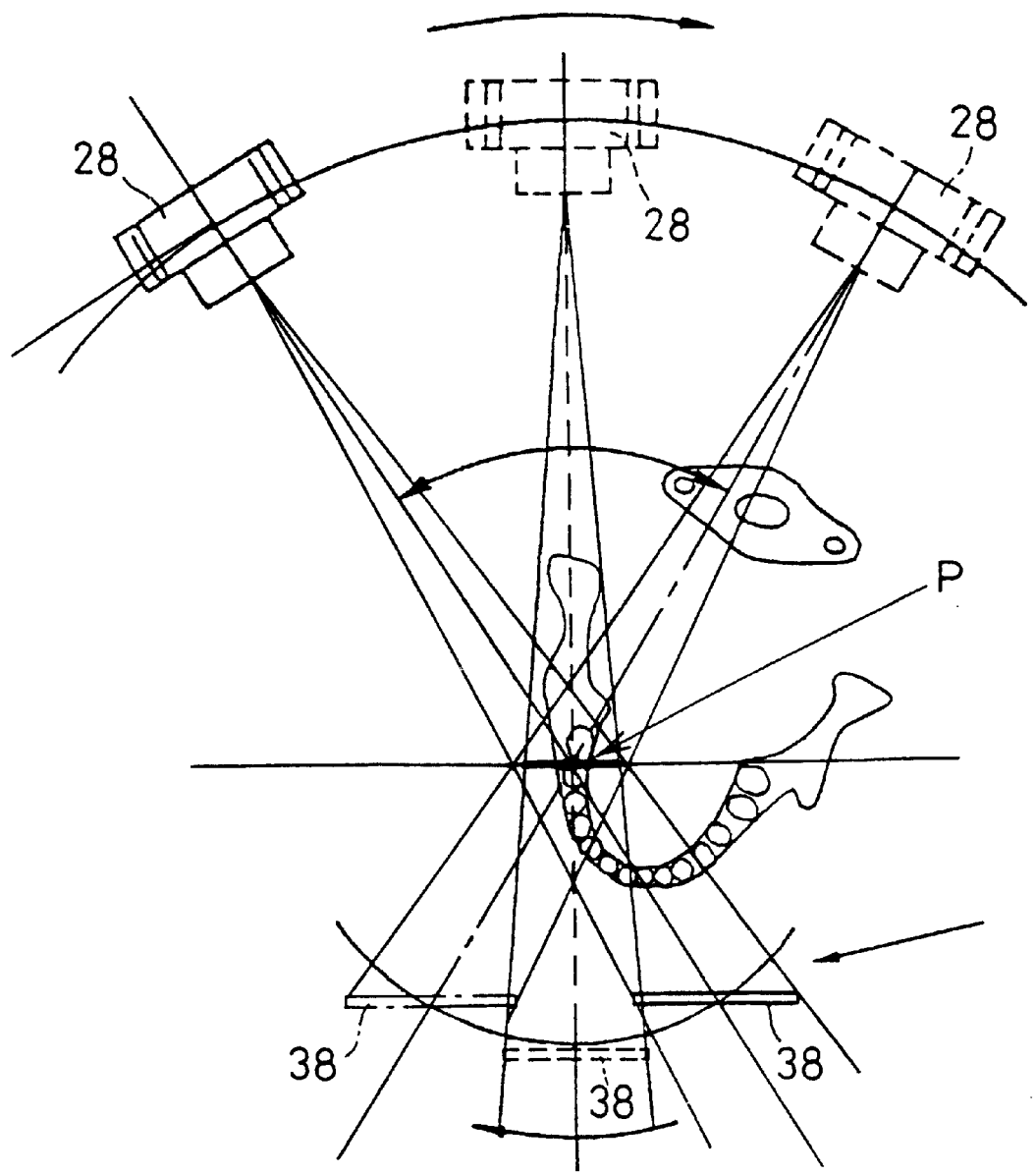
FIG. 12 is a diagram illustrating loci of an X-ray tube and an image sensor in another example of a linear X-ray imaging apparatus.

FIG. 12 shows another embodiment in which the invention is applied to a dental linear X-ray imaging apparatus. In the embodiment, the X-ray tube 28 and the image sensor 38 are revolved in opposite directions while maintaining their opposed state. During this revolution, X-rays emitted from the X-ray tube 28 always irradiate the center of the plane P and the image sensor 38 is moved so as to always maintain its parallel state with respect to the plane P. In the embodiment, the driving motor of the driving means is configured by the motor 42 (see FIG. 2) which rotates the supporting means. In order to always make the image sensor 38 parallel with the plane P, a motor or a mechanical linkage mechanism which is not shown is used.

In the X-ray imaging apparatuses shown in FIGS. 10 to 12, the mechanism for moving the X-ray tube 28 and the image sensor 38 may be realized any one of various known mechanisms.

In the embodiments described above, the obstacle is configured by the vertebrae cervicales. In the tooth and jaw region, a metal fitted article such as an implant, a crown, silver amalgam, or filling of a metal compound functions as an obstacle which largely absorbs X-rays. Even when such a fitted article exists, therefore, a clear X-ray imaging process can be conducted according to the invention.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An X-ray imaging apparatus comprising:
   an X-ray source for generating X-rays;
   X-ray imaging means for detecting X-rays having passed through an object and outputting an image signal;
   supporting means for supporting the X-ray source and the X-ray imaging means so that the X-ray source and the X-ray imaging means are opposed to each other across the object;
   a driving source for moving the supporting means in a predetermined direction;
   imaging sensitivity adjusting means for adjusting the X-ray imaging means in imaging sensitivity; and
   controlling means for controlling the imaging sensitivity adjusting means on the basis of the image signal outputted from the X-ray imaging means; and
   wherein the X-ray source is composed of an X-ray tube provided with X-ray tube current adjusting means for adjusting a current supplied to the X-ray tube and/or X-ray tube voltage adjusting means for adjusting a voltage applied to the X-ray tube, which are controlled by the controlling means, and the control means controls first the imaging sensitivity adjusting means on the basis of the image signal from the X-ray imaging means and controls the X-ray tube current adjusting means and/or the X-ray tube voltage adjusting means when the image signal is out of an adjustment range of the imaging sensitivity adjusting means.

2. The X-ray imaging apparatus of claim 1, further comprising, in relation to the driving source, driving speed adjusting means for adjusting a driving speed of the driving source, which is controlled by the controlling means,
   wherein the controlling means first controls the imaging sensitivity adjusting means on the basis of the image signal from the X-ray imaging means, controls the X-ray tube current adjusting means and/or the X-ray tube voltage adjusting means when the image signal is out of a predetermined adjustment range of the imaging sensitivity adjusting means, and controls the driving speed adjusting means when the image signal is out of a combination adjustment range of the predetermined adjustment ranges of the imaging sensitivity adjusting means, and the X-ray tube current adjusting means and/or the X-ray tube voltage adjusting means.

3. An X-ray imaging apparatus comprising:
   an X-ray source for generating X-rays;
   X-ray imaging means for detecting X-rays having passed through an object and outputting an image signal;
   supporting means for supporting the X-ray source and the X-ray imaging means so that the X-ray source and the X-ray imaging means are opposed to each other across the object;
   a driving source for moving the supporting means in a predetermined direction;
   imaging sensitivity adjusting means for adjusting the X-ray imaging means in imaging sensitivity; and
   controlling means for controlling the imaging sensitivity adjusting means on the basis of the image signal outputted from the X-ray imaging means; and
   wherein the driving source further comprises a driving speed adjusting means for adjusting a driving speed of the driving source, which is controlled by the controlling means, and the controlling means first controls the imaging sensitivity adjusting means on the basis of the image signal from the X-ray imaging means, and controls the driving speed adjusting means when the image signal is out of the predetermined adjustment range of the imaging sensitivity adjusting means.

4. An X-ray imaging apparatus comprising:
   an X-ray source for generating X-rays;
   X-ray imaging means for detecting X-rays having passed through an object and outputting an image signal;
   supporting means for supporting the X-ray source and the X-ray imaging means so that the X-ray source and the X-ray imaging means are opposed to each other across the object;
   a driving source for moving the supporting means in a predetermined direction;
   imaging sensitivity adjusting means for adjusting the X-ray imaging means in imaging sensitivity; and
   controlling means for controlling the imaging sensitivity adjusting means on the basis of the image signal outputted from the X-ray imaging means; and
   wherein the X-ray source is composed of an X-ray tub, which is provided with X-ray tube current adjusting means for adjusting a current supplied to the X-ray tube an/or X-ray tube voltage adjusting means for adjusting a voltage applied to the X-ray tube, the driving source further comprises a driving speed adjusting means for adjusting a driving speed of the driving source, and the controlling means simultaneously controls the imaging sensitivity adjusting means, the X-ray tube current adjusting means and/or the X-ray tube voltage adjusting means, and the driving speed adjusting means, on the basis of the image signal from the X-ray imaging means.

5. An X-ray imaging apparatus comprising:

an X-ray source for generating X-rays;

X-ray imaging means for detecting X-rays having passed through an object and outputting an image signal;

supporting means for supporting the X-ray source and the X-ray imaging means so that the X-ray source an the X-ray imaging means are opposed to each other accross the object;

a driving source for moving the supporting means in a predetermined direction;

imaging sensitivity adjusting means for adjusting the X-ray imaging means in imaging sensitivity; and controlling means for controlling the imaging sensitivity adjusting means on the basis of the image signal outputted from the X-ray imaging means; and wherein the driving source further comprises a driving speed adjusting means for adjusting a driving speed of the driving source, and the controlling means simultaneously controls the imaging sensitivity adjusting means and the driving speed adjusting means on the basis of the image signal from the X-ray imaging means.

* * * * *